(12) United States Patent
Schempp et al.

(10) Patent No.: US 7,687,083 B2
(45) Date of Patent: Mar. 30, 2010

(54) **PHARMACEUTICAL COMPOSITIONS COMPRISING OLD MAN'S BEARD (*USNEA BARBATA*) AND ST. JOHN'S WORT (*HYPERICUM PERFORATUM*) AND THEIR USE**

(75) Inventors: Christoph Mathis Schempp, Freiburg (DE); Andrea Jocher, Freiburg (DE); Kathrin Engel, Umkirch (DE); Constance Huyke, Freiburg (DE)

(73) Assignee: Universitatsklinikum Freiburg (DE)

( * ) Notice: Subject to any disclaimer, the term of this patent is extended or adjusted under 35 U.S.C. 154(b) by 343 days.

(21) Appl. No.: 11/578,962

(22) PCT Filed: Apr. 7, 2005

(86) PCT No.: PCT/EP2005/003657

§ 371 (c)(1),
(2), (4) Date: Nov. 9, 2006

(87) PCT Pub. No.: WO2005/099728

PCT Pub. Date: Oct. 27, 2005

(65) Prior Publication Data

US 2008/0233145 A1    Sep. 25, 2008

(30) Foreign Application Priority Data

Apr. 19, 2004   (EP) .................................. 04009213

(51) Int. Cl.
*A61K 36/38*   (2006.01)
*A61K 36/00*   (2006.01)

(52) U.S. Cl. ...................................... 424/730; 424/725

(58) Field of Classification Search ....................... None
See application file for complete search history.

(56) References Cited

FOREIGN PATENT DOCUMENTS

| DE | 101 31 641 A1 | 6/2002 |
|---|---|---|
| WO | WO 02/094300 A | 11/2002 |

OTHER PUBLICATIONS

Dr. Karl W. Quirin, "CO2-extracts of Usnea Lichen and St. John's Wort as anti-microbial multifunctional ingredients for natural cosmetics", Cosmetics and Toiletries Manufacture. pp. 43-48 (2002).
Publication No. 06-345625, "Hair Nourishing and Growing Agent", Patent Abstracts of Japan (Dec. 20, 1994).
Madamombe, I. T. et al., "Evaluation of Antimicrobial Activity of Extracts from South African Usnea Barbata", Pharmaceutical Biology, vol. 41, No. 3, pp. 199-202 (May 2003).

*Primary Examiner*—Patricia Leith
(74) *Attorney, Agent, or Firm*—Chalin A. Smith; Smith Patent Consulting, LLC

(57) ABSTRACT

Pharmaceutical compositions of *Usnea barbata* and the use thereof for the treatment of skin diseases are disclosed. A preferred composition is the combination with an extract of *Hypericum perforatum*. The extracts are obtained by supercritical high-pressure extraction with spring carbon-dioxide. A preferred form of preparation is the homogenization of 6% by weight of an extract of *Usnea barbata*, containing 96% of usnic acid, and 40% by weight of an extract of *Hypericum perforatum*, containing 39% of hyperforin, together. The pharmaceutical composition leads to a potentiation of the anti-inflammatory and antimicrobial effects of the extracts and to stabilization of the hyperforin. The combination is suitable for the external and internal treatment of various skin diseases, in particular skin inflammations and skin ageing, and for the treatment of skin infections with pityrosporon yeast fungi, acne and rosacea.

15 Claims, 7 Drawing Sheets shows the inhibition of the UV-induced increase of matrix metalloproteinase-1 (MMP-1) by Usnea extract and the potentiation of the effect by combination of Usnea extract and Hypericum extract.

HPLC chromatogram of an enriched old man's beard $CO_2$ extract having a content of 96.8% of total usnic acids.

HPLC chromatogram of a St. John's Wort $CO_2$ extract having a content of 40% of total hyperforins.

HPLC chromatogram of a combined old man's beard – St. John's Wort $CO_2$ extract Usninsäurederivate = Usnic acid derivatives Luminisenz = luminescence
Extrakt = extract Investigation of Usnea extract (5%) in comparison with Dermatop® ointment (Prednicarbate) in the UV erythema test Erythem-Index = erythema index
Unbehandelt = untreated
Vehikel = vehicle
Prednicarbat = prednicarbate Figure 6 shows the dose-dependent inhibition of the UV-induced prostaglandin synthesis by Usnea extract.

Kontrolle ohne AA = control without AA
Kontrolle mit AA = control with AA
Bestrahlung mit UVB = exposure to UVB Figure 7 shows the inhibition of the UV-induced increase of matrix metalloproteinase-1 (MMP-1) by Usnea extract and the potentiation of the effect by combination of Usnea extract and Hypericum extract.
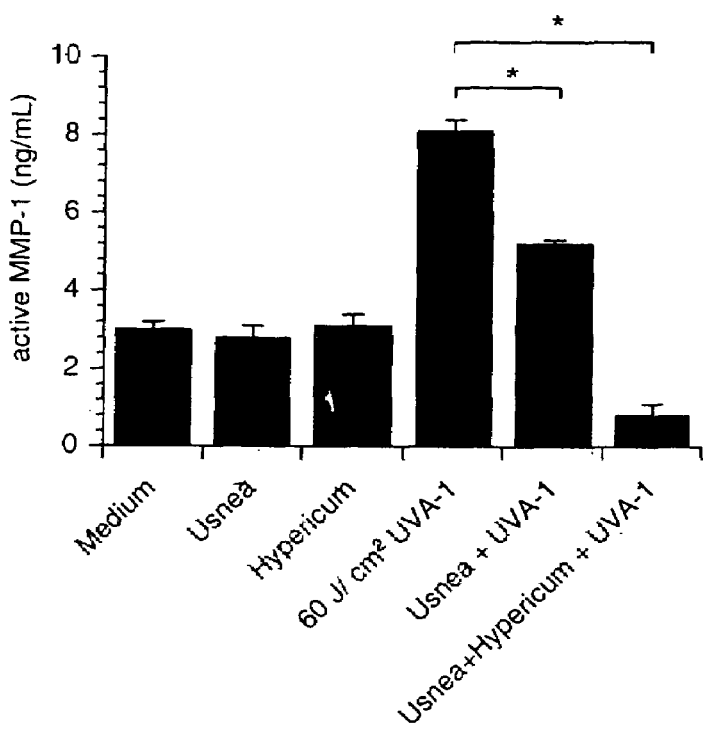

PHARMACEUTICAL COMPOSITIONS COMPRISING OLD MAN'S BEARD (*USNEA BARBATA*) AND ST. JOHN'S WORT (*HYPERICUM PERFORATUM*) AND THEIR USE

This application is a Rule 371 U.S. National Phase Filing of PCT/EP05/003657, filed Apr. 7, 2005, which, in turn, claims priority to European Patent Application No. 04.009213.2 filed Apr. 19, 2004, the contents of which are incorporated by reference herein in their entirety.

The present invention relates to pharmaceutical compositions comprising constituents of *Usnea barbata*, which can be used in particular in the case of those skin diseases where inflammations and accelerated skin ageing occur due to the action of sunlight and oxygen radicals. The pharmaceutical compositions can also be used in the case of those skin diseases where various yeast fungi and bacteria contribute to the genesis of these diseases.

The skin diseases of the seborrhoeal group include acne, rosacea and seborrhoeal eczema. Various bacteria, in particular propionibacterium acnes or corynebacteria, and yeast fungi, in particular pityrosporon, contribute to the genesis of these skin diseases. In addition, the diseases of the seborrhoeal group are characterised by inflammation of the hair follicles and of the surrounding tissue. These skin diseases have a considerable adverse effect on the quality of life of the affected persons. Mild to moderately severe forms are usually treated with various local therapeutic agents. The customary treatment agents include peelings (e.g. benzoyl peroxide, glycolic acid), antibiotics (e.g. erythromycin, clindamycin, tetracycline) and vitamin A acid derivatives.

These customary active substances are problematic for various reasons: the local application of antibiotics is effective, but resistances may occur. These in turn are problematic since the antibiotics are also used in the case of other severe infections. Benzoyl peroxide leads to skin irritations and also bleaches laundry. Vitamin A acid also leads to pronounced skin irritations. The substances used have no significant anti-inflammatory effect.

Skin diseases of the seborrhoeal group (acne) are frequently very problematic. Since the skin irritations occur especially on the face, this can lead to severe psychological disturbances. There is therefore a need for effective pharmaceutical compositions which firstly effectively and quickly eliminate the undesired symptoms and secondly have side effects which are as slight as possible.

The prior art discloses various preparations which contain plant constituents as active substances.

WO02/094300, "Herbal Compositions for the Treatment of mucosal Lesions", describes therapeutic compositions which are useful in the control of inflammatory mucosal diseases of viral origin. The compositions contain extracts of the plants *Echinacea purpurea* and *Sambucus nigra* and extracts of at least one further plant selected from any group which consists of *Hypericum perforatum, Commiphora molmol* and *Centella asiatica*. This base composition may contain further plant extracts consisting of the group of *Uncaria tomentosa, Thymus vulgaris, Matricaria recutita, Salix alba, Calendula officinalis, Usnea barbata, Ligusticum porterii, Gaultheria procumbens, Camellia sinensis, Vaccinium myrtillus, Melissa officinalis, Allium sativum* and *Crameria triandra*. Of the possible combinations of 19 different plants, it is not evident which combination has a particular effect. Furthermore, the group of seborrhoeal diseases and especially acne are not mentioned at any point in WO02/094300. Rather, the discussion is of virally caused inflammatory mucosal diseases, of other inflammatory mucosal diseases and of reactions to insect bites.

JP 52468876 states that lichen extract can have antibacterial effects against gram-positive bacteria.

WO 02/051427 describes stable extracts of *Hypericum perforatum* and pharmaceutical compositions which contain this extract, and topical drugs for the treatment of acne, atopic dermatitis, psoriasis, etc.

EP 1131063 describes a use of hyperforin from *Hypericum perforatum* as an antibacterial ingredient which is suitable for the treatment of skin diseases.

According to the invention, it was found that the combination of extracts of *Usnea barbata* and *Hypericum perforatum* contributes to an unexpected potentiation of the anti-inflammatory effect of the individual components. The combination of the extracts also leads to complete inhibition of the UV-induced activation of collagenase. Particularly surprising is that the combination of the extracts of *Usnea barbata* and *Hypericum perforatum* leads to an unexpected stabilisation of hyperforin which is important for the effect. In this way, the anti-inflammatory and antimicrobial effects of the two components can be combined and potentiated.

Exposure to Ultraviolet B (UVB) radiation leads to reddening and inflammation of the skin, which is referred to as sunburn (Dermatitis solaris) when it is pronounced. An important factor for the genesis of sunburn is the production of prostaglandin $E_2$ ($PGE_2$) by keratinocytes. Oxygen radicals play an important role in UV-induced inflammation. Through activation of the epidermal growth factor (EGF) receptor, they lead to an increase in cyclooxygenase-2 (COX-2). COX-2 catalyses the formulation of $PGE_2$ (Ashida et al., Experimental Dermatology 2003:12:445-452).

According to the invention, an effective formulation which can inhibit the UV-induced $PGE_2$ synthesis is disclosed. It was surprisingly found that an extract of *Usnea barbata* having a defined content of usnic acid inhibits the UV-induced synthesis of $PGE_2$ in keratinocytes.

UV exposure of the skin also leads to accelerated skin ageing. Owing to the formation off oxygen radicals and proinflammatory cytokines, activation of the enzyme matrix metalloproteinase-1 (MMP-1) is induced in the fibroblasts in the connective tissue of the skin (Scharfetter et al., Archives of Dermatological Research 1991: 283: 506-511). MMP-1 is also referred to as collagenase. The collagenase leads to accelerated degradation of collagen-1, which is an important constituent of the connective tissue of the skin. Activation of collagenase results in premature, accelerated skin ageing.

According to the invention, an effective formulation which can inhibit the UV-induced MMP-1 collagenase activation is provided. It was surprisingly found that the UV-induced increase of collagenase in fibroblasts can be inhibited by an extract of *Usnea barbata*. This effect could be further potentiated by the combination of the extract of *Usnea barbata* with an extract of *Hypericum perforatum*.

The present invention relates to pharmaceutical compositions which are characterized in that they contain 0.001-20% by weight and preferably 0.01-10% by weight of a $CO_2$ extract of *Usnea barbata* and 0.01-80% by weight, preferably 0.01-20% by weight, of a $CO_2$ extract of St. John's Wort (*Hypericum perforatum*). The stated percentages by weight are based on the final pharmaceutical compositions.

According to the invention, a $CO_2$ extract of *Usnea barbata* (old man's beard) is used. The main constituent of the active components of the extract is usnic acid, which occurs in two enantiomeric forms, namely (+)-9bR-usnic acid and (−)-9bS-usnic acid. It is assumed that, owing to its biocidal effect in pharmacy and cosmetics, the (+)-usnic acid in particular is preferably used. In the present case, the racemate or (+)-9bR-usnic acid is preferably used.

Processes for the isolation of usnic acid from lichens (*Usnea barbata*) are disclosed in the prior art (for example DE 32 13 095). In these extraction processes, organic solvents or alcohol are employed.

A disadvantage of these methods is that the extraction does not result in any depletion of harmful substances. This is important since old man's beard varieties can enrich harmful substances from the air and from precipitates (for example heavy metals). In the present invention, those extracts of *Usnea barbata* which are prepared by high-pressure extraction with $CO_2$ are therefore used. An advantage of this extraction method is that no heavy metals and solvent residues remain behind. By means of the $CO_2$ extraction, the usnic acid can be purified to a virtually pure form.

Extracts of *Usnea barbata* which were prepared by high-pressure extraction with $CO_2$ can be used. An advantage of this extraction method is that no solvent residues remain behind. After the $CO_2$ extraction, the usnic acid can be purified to a virtually pure form. The extracts are formulated with vegetable oil and emulsifier and are commercially available (for example Flavex® Naturextrakte GmbH). By adding pharmaceutically acceptable additives, the desired content of active substance can be adjusted.

The extracts of lichens used contain 2-7, preferably 3-5 and particularly preferably about 4% by weight of usnic acid. In the $CO_2$ extract, derivatives of usnic acid are also present as further lichen acid in an amount of up to 0.5% by weight, preferably up to 0.2% by weight and particularly preferably up to 0.1% by weight.

The *Usnea barbata* extract preferably used according to the invention is prepared by a special process with spring carbon-dioxide under high pressure. The drug (plant material) is extracted with supercritical $CO_2$ after prior conditioning. The crude extract thus obtained contains about 60% of usnic acid. In a second purification step, the ineffective or undesired lipophilic impurities, such as volatile oils, fatty acids, hydrocarbons, chlorophylls and other lichen acids, are substantially separated off from the usnic acid.

This gives the $CO_2$ extract preferred according to the invention and having a content of about 92+/−5% of usnic acids, which is obtained as a pale yellowish to slightly greenish powder, while the components separated from the crude extract form a dark green viscous oil which is discarded. It is thus ensured that any existing, potentially allergenic lichen acids of the depsidon type or aliphatic lichen acids which are characterized by the presence of one or two carboxyl groups are substantially separated off from the natural usnic acid, a dibenzofuran derivative without a carboxyl group. An HPLC chromatogram of the purified old man's beard $CO_2$ extract comprising 96.8% of total usnic acids is shown in FIG. 1, the total usnic acids comprising 88.3% of (+/−)-usnic acid and 8.5% of a usnic acid derivative (isousnic acid).

For the use in pharmaceutical preparations, it may be necessary to use the active substances in low concentrations. In this case, the extracts are diluted with suitable diluents, such as, for example, triglycerides and emulsifiers, to lower active substance concentrations (for example 4% of usnic acid, 10% of hyperforin).

Although allergies to the lichen acids are described, the sensitizing potency of the lichens is said to be low and is due to lichen acids other than usnic acid. Purified $CO_2$ extracts which have a total usnic acid content of at least 85% are therefore preferably used. These $CO_2$ extracts preferably comprise not more than 0.1% by weight and particularly preferably less than 0.1% by weight of other lichen acids, which may be responsible for allergies.

The literature states that *Usnea* species and usnic acid have a broad antibacterial spectrum and that they are therefore suitable for the treatment of surface infections and skin ulcers. The overview by Cocchietto M et al. (2002, Naturwissenschaften 89: 137-146) summarises the knowledge relating to the antibacterial effects of usnic acid.

The other essential constituent of the pharmaceutical compositions according to the invention is an extract of St. John's Wort (*Hypericum perforatum*). St. John's Wort is used in large amounts and has been used for a long time in phytomedicine. A substantial constituent of St. John's Wort is the active substance Hyperforin.

Since the effects of Hyperforin in St. John's Wort are particularly important for the use according to the invention, a $CO_2$ extract of *Hypericum perforatum* is used. $CO_2$ extracts of *Hypericum perforatum* contain, as active constituents, virtually only hyperforins from the group consisting of the acylphloroglucinols, but virtually no hypericins from the group consisting of the naphthodianthrones. $CO_2$ extracts also contain no flavonoglycosides, proanthocyanidines, chlorophylls and chlorogenic acids.

Hyperforin is an antibacterial ingredient from St. John's Wort (*Hypericum perforatum*), which is suitable for the treatment of inflammatory skin diseases (EP 1 131 063). Owing to its pronounced lipophilicity, this ingredient is readily soluble only in nonpolar solvents and fats. On emulsification in aqueous solutions, rapid degradation of Hyperforin occurs. This problem can be avoided by preparing various salts of hyperforin. In this form, Hyperforin is stable on storage (WO 99/41220). However, if the Hyperforin salts are brought into an aqueous solution, free hyperforin dissociates and is likewise rapidly degraded.

According to the invention, a $CO_2$ extract of *Hypericum perforatum* is preferably used. An extract is prepared from the tips of twigs and blooms of *Hypericum perforatum* by high-pressure extraction with spring carbon dioxide. It is known that the blooming tips of twigs contain predominantly hypericins in the early vegetation period whereas the hyperforins predominate in the later stage of flowering. If a raw material which is optimised in this respect and which is prepared in a gentle manner and conditioned for the extraction is used, it is possible to obtain $CO_2$ extracts which have a total hyperforin content of up to 40%. The total hyperforin usually consists of 82-86% of hyperforin and 14-18% of adhyperforin. An HPLC chromatogram of a high-quality $CO_2$ extract comprising 40% of total hyperforin, comprising 34.1% of hyperforin and 5.9% of adhyperforin, is shown in FIG. 2.

In a preferred embodiment, the St. John's Wort extract used according to the invention contains no detectable hypericin. With the use of HPLC under standard conditions for analytical detection, no hypericin can be detected in the St. John's Wort extract used according to the invention.

In the present invention, it was surprisingly found that the combination of the two extracts exhibits a synergistic effect which goes beyond the simple addition of the activities of the individual extracts.

Hyperforin is a substance which is unstable per se. Surprisingly, it was found that the *Usnea barbata* extract used according to the invention contributes to a substantial stabilisation of hyperforin.

The combination of the *Hypericum* extract with the *Usnea* extract increases the anti-inflammatory effect of the individual components by about ten-fold. The combination of the *Hypericum* extract adjusted with respect to hyperforin and of a *Usnea* extract adjusted with respect to usnic acid thus provides an unexpected pharmaceutical improvement.

The present invention relates to pharmaceutical compositions which are characterized in that they contain 0.001-20% by weight of a $CO_2$ extract of *Usnea barbata* and 0.01-80% by weight, preferably 0.01 to 20% by weight, of a $CO_2$ extract of *Hypericum perforatum*.

A pharmaceutical composition preferred according to the invention contains 0.11-10% by weight of the extract of *Usnea barbata* and 10-60% by weight of the extract of *Hypericum perforatum*. Particularly preferably, 6% by weight of the extract of *Usnea barbata* and 40% by weight of the extract of *Hypericum perforatum* are combined.

A particularly preferred preparation form is the homogenisation of 6% by weight of the extract of *Usnea barbata* and 40% by weight of the extract of St. John's Wort in a colloid mill, which has the following advantages: the proven stabilising effect of the usnic acid on the *Hypericum* extract is expediently utilised at as early a time in the preparation as possible. For this purpose, the enriched usnic acid of the old man's beard extract, a slightly soluble powder, is digested by incorporation into the formulation with addition of a vegetable oil component and emulsifier component. In the colloid mill, usnic acid particles of less than 5 μm (micron) are achieved under gentle conditions. The amounts of hyperforin and usnic acid active substances which correspond to the mixed individual components are measured analytically accurately in the homogenized material, i.e. no degradation reaction is observable during the preparation of the *Usnea-Hypericum* concentrate. With the homogenised material, accelerated kinetics of dissolution and a more uniform distribution of the active substances in the end product are achieved. This gives a concentrate which is an ideal preformulation for processing to give preparations according to the invention for topical treatment. It in no way limits the end formulation and can be used both in hydrophilic and in lipophilic end products. An HPLC chromatogram of such an extract is shown in FIG. 3.

The *Usnea-Hypericum* concentrate according to the invention is advantageously used in a concentration of 0.01% to 10% in topical bases. A concentration of 0.5% to 5% is preferred and the concentration of about 2% is most preferred. This corresponds to a hyperforin concentration of about 0.3% and a usnic acid concentration of about 0.1% in the end product. The stated percentages by weight are based on the final preparation.

Especially in an aqueous gel base, the *Usnea-Hypericum* concentrate is a particularly suitable preparation for the treatment of acne and impure skin. A further field of use of the *Usnea-Hypericum* concentrate is the prevention of UV-induced inflammation and skin ageing.

The *Usnea-Hypericum* concentrate can advantageously be incorporated into other fat-free gel bases which are generally known to the person skilled in the art. Owing to the lipophilicity of the components, however, the incorporation of the components into lipid phases is also possible, for example in the form of lipogels, creams, lotions and ointments.

The *Usnea-Hypericum* concentrate is suitable not only for the treatment of microbial skin diseases, such as acne and impure skin. Owing to the pronounced antiinflammatory effect independent thereof, the combination of the extracts is also outstandingly suitable for the treatment of inflammatory skin diseases, such as eczema, lichen rubber and psoriasis, in particular if the face and the hair-covered head are affected.

In addition to the *Usnea-Hypericum* concentrate, the pharmaceutical composition also contains additives which are added depending on the chosen pharmaceutical formulation.

In addition to the base substances for gels, ointments, lotions, tinctures, etc., the pharmaceutical compositions can optionally contain preservatives, antioxidants, odorous substances, colorants and the like. It is self-evident that all individual components must sum to 100% by weight of the final preparation.

In a preferred embodiment, the pharmaceutical compositions according to the invention are provided as topical formulation forms. Topical dosage forms are used especially in the local treatment of diseases of the skin and more rarely in the case of systemic diseases.

A multiplicity of topical dosage forms is known to the pharmacist. Customary embodiments of a topical formulation for dermatological diseases are ointments. In these, the pharmacologically active substance is dissolved or suspended in a semisolid ointment base. Usually, these are hydrophobic, spreadable ointments which prevent the evaporation of water from leaving the skin. Particularly in the treatment of acne, however, ointments are not preferred because the ointment base may promote the occurrence of skin impurities. However, in the case of other diseases, for example psoriasis, it may certainly be advantageous to incorporate the pharmaceutical composition according to the invention into an ointment base. The ointment base is frequently formed by liquid, semisolid or even solid hydrocarbons, which are usually obtained from mineral oil. However, natural waxes (for example beeswax or jojoba oil) or synthetic waxes, such as cetyl ester waxes, can also be used. Organic oils, in particular olive oil or cotton seed oil, can also be incorporated into the ointments. The consistency of the final ointment can be influenced by the mixture of the individual constituents.

In a further embodiment, the *Usnea-Hypericum* concentrate according to the invention can be incorporated into creams. These are semisolid emulsions which are more fluid than ointments and are easier to distribute over the skin. The base constituents of the creams may absorb relatively small amounts of water and can be processed to give emulsions. As a rule, such creams can be washed off with water and do not block the pores of the skin. They are not greasy and, on application to the skin, have an acceptable appearance. Usually, creams consist of two phases, namely an oil-like internal phase which preferably consists of hydrocarbons and high molecular weight alcohols or fatty acids. Furthermore, the creams contain an aqueous phase which frequently contains preservatives, humectants and buffers. Finally, the creams usually comprise one or more emulsifiers. Frequently, anionic, surface-active agents, such as sodium laurylsulphate or triethanolamine stearate, and nonionic surfactants, such as, for example, ethylene oxide derivatives, are used as emulsifiers. Cationic surfactants, such as quaternary ammonium salts, are less preferred since they can frequently lead to skin irritations.

In order to be able to dissolve the pharmaceutically active substances more readily, the creams may contain liquid and waxy components, such as, for example, polyethylene glycol.

In a preferred embodiment, the pharmaceutical compositions according to the invention are incorporated into aqueous gels. In the case of the aqueous gels, a liquid, aqueous internal phase is immobilised in a three-dimensional matrix. The system is provided by colloidal dispersion of small inorganic or large organic molecules in an aqueous medium. Nonionic or anionic cellulose derivatives, such as, for example, sodium carboxymethylcellulose, acidic carboxyvinyl polymers or other hydrophilic colloids, such as magnesium aluminium silicate, sodium alginate or tragacanth gum, are used as gel-forming substances.

The *Usnea-Hypericum* concentrate according to the invention can also be used in lotions or solutions, where propylene glycol can preferably be used as an emulsifier. By using 5-10% of propylene glycol, it is possible to emulsify the lipophilic extract in the gel.

In another embodiment, the *Usnea-Hypericum* concentrate according to the invention can also be used as a powder. Particularly when used on greasy skin, it may be advantageous to formulate the pharmaceutical composition as a powder, such powders frequently being prepared with an inorganic base. Preferably used powder bases are pulverulent, absorptive non-toxic substances having good coverage and adhering to the skin. Silica, precipitate chalk, magnesium carbonate, zinc oxide and talc and mixtures of these base substances are preferably used. In the case of the pharmaceutical formulation, it should be noted that the *Usnea-Hypericum* concentrate according to the invention must be present in a form in which it can be adsorbed or absorbed by the powder bases. For this purpose, for example, a part of the *Usnea-Hypericum* concentrate can be dissolved in 9 parts of 79% ethanol and sprayed onto the silica.

Finally, the *Usnea-Hypericum* concentrate according to the invention can also be provided in the form of an aqueous gel which acquires a solid structure by addition of suitable substances so that transparent pens which contain the pharmaceutical composition and can be used for covering special skin impurities are preferably provided. Such pens preferably contain polyhydric aliphatic alcohols having preferably 2-6 carbon atoms, such as ethylene glycol, propylene glycol, trimethylene glycol, glycerol and mixtures of these compounds. For stiffening the aqueous gel, it is also possible to use saturated or unsaturated higher fatty acids having preferably 14 to 22 carbon atoms. Examples of these are myristic acid, palmitic acid, stearic acid, oleic acid, linolenic acid or mixtures of these fatty acids.

In the case of the pharmaceutical formulations, incorporation of the *Usnea-Hypericum* concentrate according to the invention into a nanoemulsion is preferred. This nanoemulsion can advantageously be incorporated into an aqueous gel base.

A preferred gel base contains Carbomer 50 000, 2-propanol, propylene glycol and water (cf. formulation example 1). The *Usnea-Hypericum* concentrate according to the invention may also advantageously be incorporated into other aqueous preparation forms, such as lotions, sprays, facial tonics and scalp emulsions. A particularly preferred aqueous solution contains the combined extract in an essence comprising octyldodecanol, 2-propanol, propylene glycol and water.

For certain formulations, it may be advantageous to add zinc sulphate heptahydrate in a concentration of 0.5-1.5%, preferably 1.0%.

Over and above the incorporation of the *Usnea-Hypericum* concentrate according to the invention into aqueous carrier systems, it is also suitable for incorporation into creams, wash lotions, lipogels and ointments, the principle compositions of which are generally known to the person skilled in the art.

The *Usnea-Hypericum* concentrate according to the invention is also suitable for internal use in the form of capsules. For this purpose, the concentrate is incorporated in suitable concentration into a high-quality vegetable oil and incorporated into opaque hard gelatine capsules in the absence of light and oxygen. The incorporation of the concentrate in the form of a microemulsion is also suitable. The administration of the concentrate in capsules is suitable for the treatment of skin diseases which are characterised by microbial infection and inflammation. The capsules are particularly suitable for the intensive internal treatment of particularly stubborn diseases of the seborrhoeal group, for example acne and rosacea.

The *Usnea-Hypericum* concentrate used is not used otherwise as an antibiotic and is free of harmful substances and preservatives. Owing to their liphophilicity, the active substances penetrate particularly well into the sebaceous glands, where they display their antimicrobial effect. If appropriate, however, the pharmaceutical preparations may also contain those substances which increase the rapid take-up of the active substances.

The pharmaceutical compositions of the present invention provide a natural product which is highly effective against the germs relevant in the seborrhoeal group and, independently thereof, additionally has an anti-inflammatory effect. The anti-inflammatory effect was detected by the proliferation test with lymphocytes, by the inhibition of UV-induced prostaglandin synthesis and in the model of the UV erythema test.

Preparations comprising *Usnea-Hypericum* concentrate thus provide a basis for the treatment of acne and similar skin diseases having a natural basis. In the *Usnea-Hypericum* concentrate used, both an excellent effect against acne bacteria and an excellent effect against pityrosporon yeast fungi are simultaneously displayed. The extract also has an anti-inflammatory effect without irritating the skin. Moreover, preparations comprising *Usnea-Hypericum* concentrate can counteract UV-induced inflammation and accelerated skin ageing.

The combination of the *Usnea-Hypericum* concentrate with a sun protection factor is particularly advantageous when used on the face. Suitable sun protection factors may be organic chemical and/or mineral UV filters and are sufficiently well known to the person skilled in the art.

In a further preferred embodiment of the invention, a $CO_2$ extract of the Ratanhia root (*Krameria lappacea*) is also added as a sun protection factor. The $CO_2$ Ratanhia extract contains no polymeric catechol tanning agents, which tend to be undesired in the case of sensitive skin, but lipophilic phenols of the neolignan and norneolignan type. The Ratanhia extract is thus a well tolerated, high-quality UVA2 and UVB filter having high photostability, which has filter activity at wavelengths of less than 340 nanometers. The transmissibility of the longer-wave UVA1 radiation in the range of 340-400 nanometers is entirely desirable in the case of many indications. The Ratanhia extract additionally promotes the antimicrobial and anti-inflammatory effect of the claimed *Usnea-Hypericum* concentrate and can make an additional contribution to the hyperforin stability by UV protection in hydrophilic end formulations. The $CO_2$ Ratanhia extract is prepared analogously to the other $CO_2$ extracts described here and contains at least 60, preferably at least 80, % by weight of active constituents.

Figure 5:
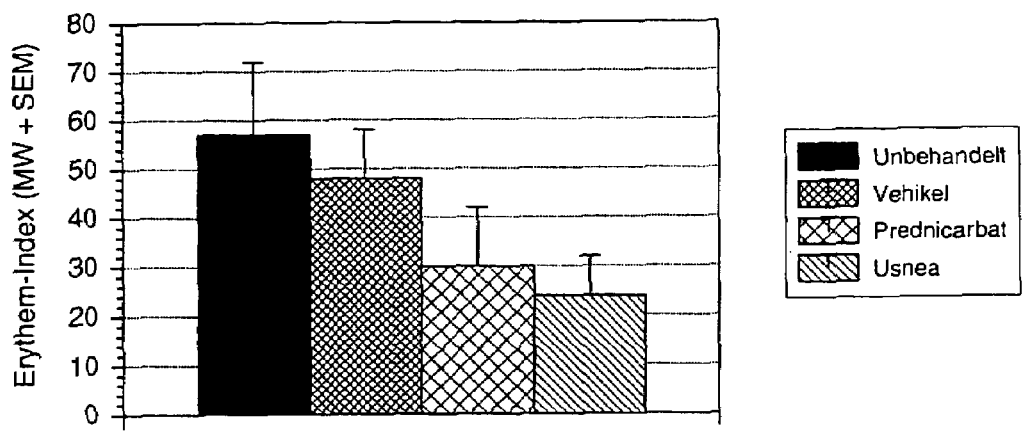

FIG. 5 shows the anti-inflammatory effect of a *Usnea* extract which was applied to the skin of the test persons in a concentration of 5% in an aqueous gel. An inflammation caused by UVB radiation can be treated by the pharmaceutical composition according to the invention. The pharmaceutical compositions according to the invention are therefore also suitable for the treatment of inflammations caused by excessive exposure to sun (sunburn).

Figure 6:
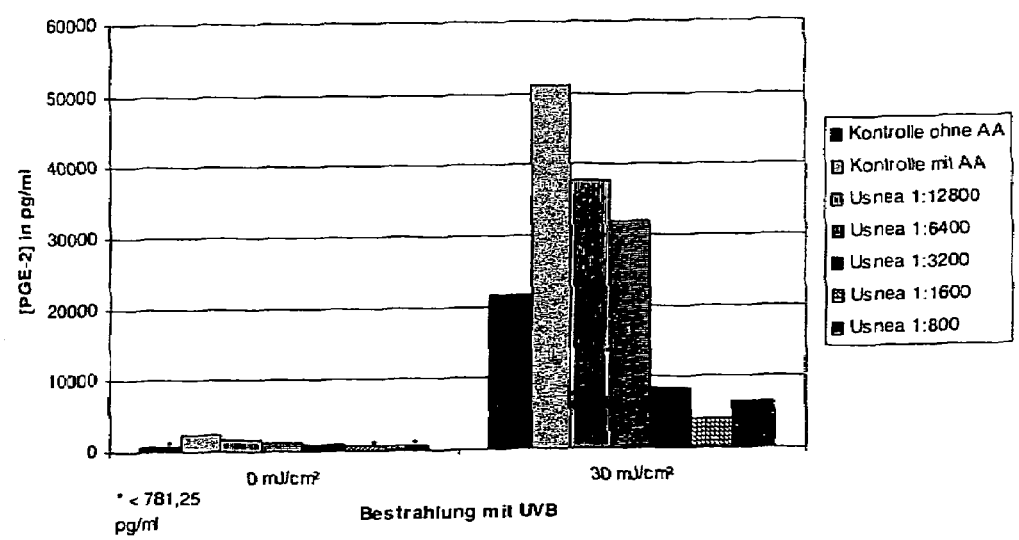

FIG. 6 shows the dose-dependent inhibition of the UV-induced prostaglandin synthesis by *Usnea* extract.

FIG. 7 shows the inhibition of the UV-induced increase of matrix metalloproteinase-1 (MMP-1) by *Usnea* extract and the potentiation of the effect by combination of *Usnea* extract and *Hypericum* extract.

The following examples are intended to explain the invention in more detail.

PREPARATION EXAMPLE 1

Aqueous Gel Comprising Propylene Glycol a) 3% of *Hypericum* extract
   2% of *Usnea barbata* extract
   gel base to 100.0
   Gel base

| | |
|---|---|
| Carbomer 50 000 | 0.5 |
| 2-propanol | 5.0 |
| Propylene glycol | 20.0 |
| Sodium hydroxide | 0.12 |
| Purified water | to 100.0 | b) 1% *Usnea-Hypericum* concentrate
   gel base to 100.0
   Gel base

| | |
|---|---|
| Carbomer 50 000 | 0.5 |
| 2-propanol | 5.0 |
| Propylene glycol | 20.0 |
| Sodium hydroxide | 0.12 |
| Purified water | to 100.0 |

PREPARATION EXAMPLE 2

Facial Tonic a) 3% of *Hypericum* extract
   2% of *Usnea barbata* extract
   1% of zinc sulphate heptahydrate
   Alcoholic essence to 100.0
   Alcoholic essence:

| | |
|---|---|
| Octyldodecanol | 18.0 |
| 2-propanol | 58.0 |
| Propylene glycol | 10.0 |
| Purified water | to 100.0 |

Extracts used:

St. John's Wort extract: "St. John's Wort $CO_2$ extract", from FLAVEX
*Usnea* extract: "*Usnea lichen* $CO_2$ extract water soluble", from FLAVEX b) 2% of *Usnea-Hypericum* concentrate
   1% of zinc sulphate heptahydrate
   Alcoholic essence to 100.0
   Alcoholic essence:

| | |
|---|---|
| Octyldodecanol | 18.0 |
| 2-propanol | 58.0 |
| Propylene glycol | 10.0 |
| Purified water | to 100.0 |

EXAMPLE 1

Antimicrobial Effect of the Old Man's Beard $CO_2$ Extract

The old man's beard $CO_2$ extract (*Usnea barbata* L.) was tested in the concentrations 1:10, 1:50, 1:100, 1:500 and 1:1000 in the agar dilution test for a number of aerobic and anaerobic bacteria. The pure substance usnic acid was tested in concentrations of 128/64/32/16/8/4/2/1/0.5/0.25 and 0.125 µg/ml. The MIC (minimum inhibitory concentration) is defined as >90% inhibition of bacterial growth after 24 h. The MBC (minimum bactericidal concentration) is defined as >90% inhibition of the growth at 48 h. It was surprisingly found that *Propionibacterium acnes* is highly sensitive to the *Usnea* extract and to usnic acid. This is shown in Table 1:

TABLE 1

Efficacy of *Usnea* extract and usnic acid on Priopionibacterium acnes

| Germ name | Old man's beard extract MIC | Old man's beard extract MBC | Usnic acid MIC | Usnic acid MBC |
|---|---|---|---|---|
| Propionibacterium acnes | 1:2500 | 1:1000 | 1 µg/ml | 4 µg/ml |

In addition, the efficacy against pityrosporon of 1% *Usnea* extract in olive oil in comparison with 1% amphotericin was investigated. For this purpose, scales of patients with seborrhoeal eczema were applied to Sabouraud agar and covered with a layer of the oil. After incubation for 4 days in an incubator, the number of colony-forming units was counted. The growth of the pityrosporon yeast fungi was inhibited completely by the *Usnea* extract and amphotericin but not by olive oil alone. This is shown in Table 2:

TABLE 2

Efficacy of *Usnea* extract on pityrosporon yeast fungi in the oil submersion test

| Germ name | 1% Old man's beard extract in olive oil | 1% Amphotericin in olive oil | Olive oil without addition |
|---|---|---|---|
| Pityrosporon ovale | 0 CFU | 1 CFU | 29 CFU |

EXAMPLE 2

Figure 1:
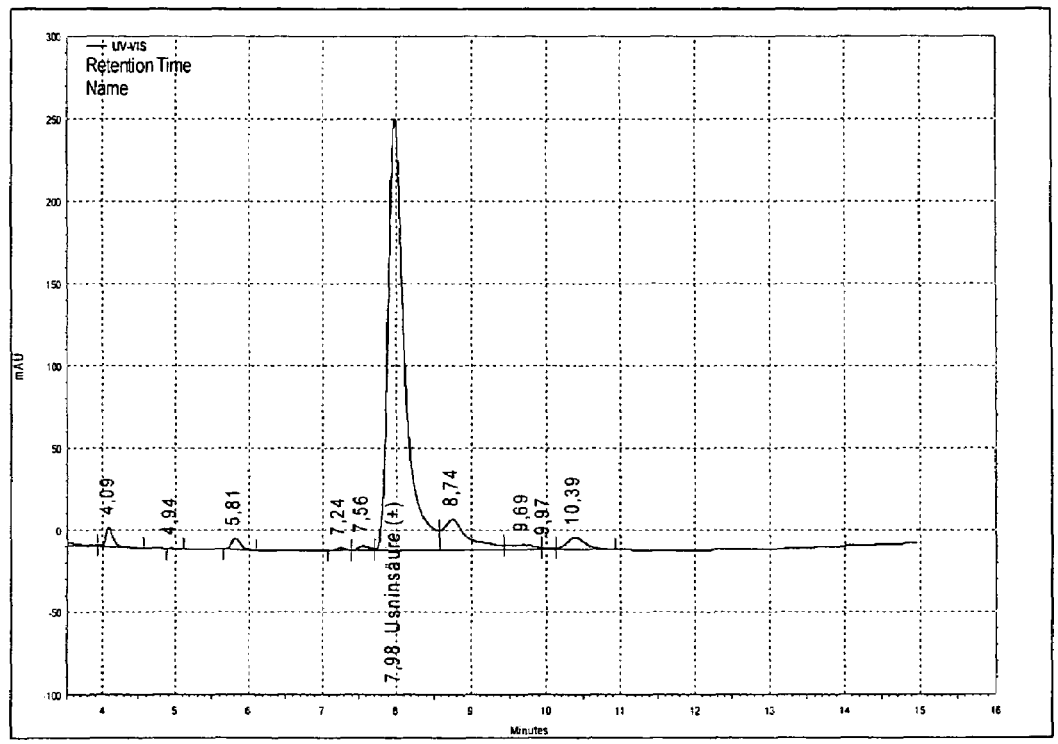
FIG. 1 shows the HPLC chromatogram of an enriched $CO_2$ extract of old man's beard having a content of about 96.8% by weight of total usnic acid.
Figure 2:
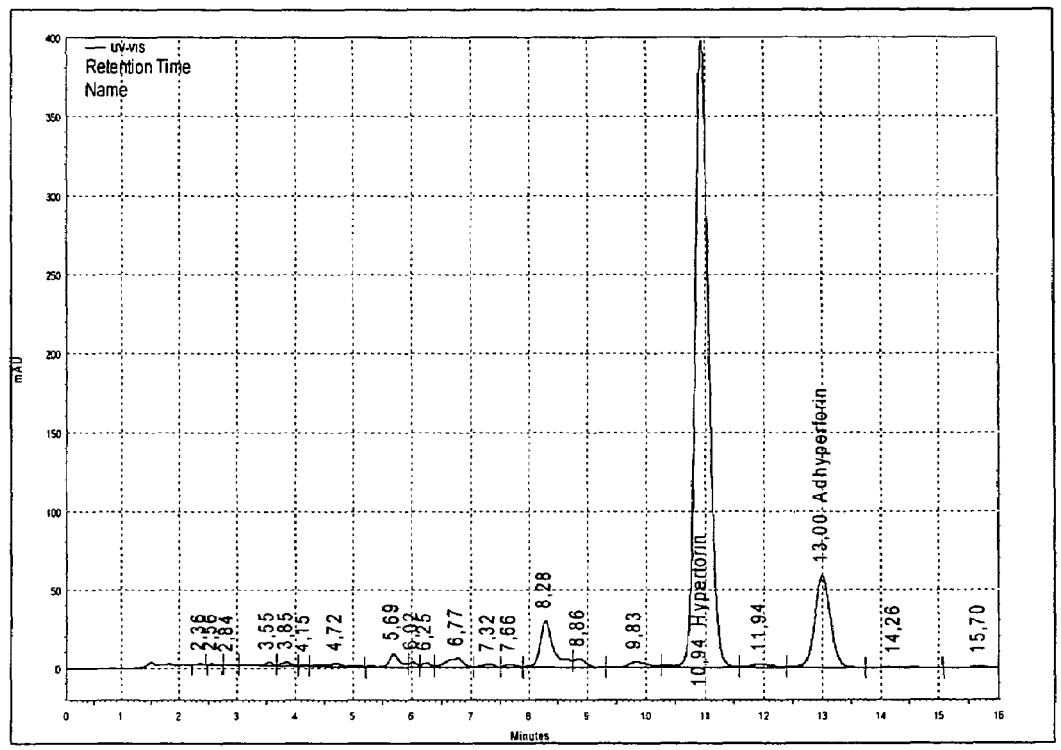
FIG. 2 shows the HPLC chromatogram of a St. John's Wort $CO_2$ extract having a content of about 40% of total hyperforins.
Figure 3:
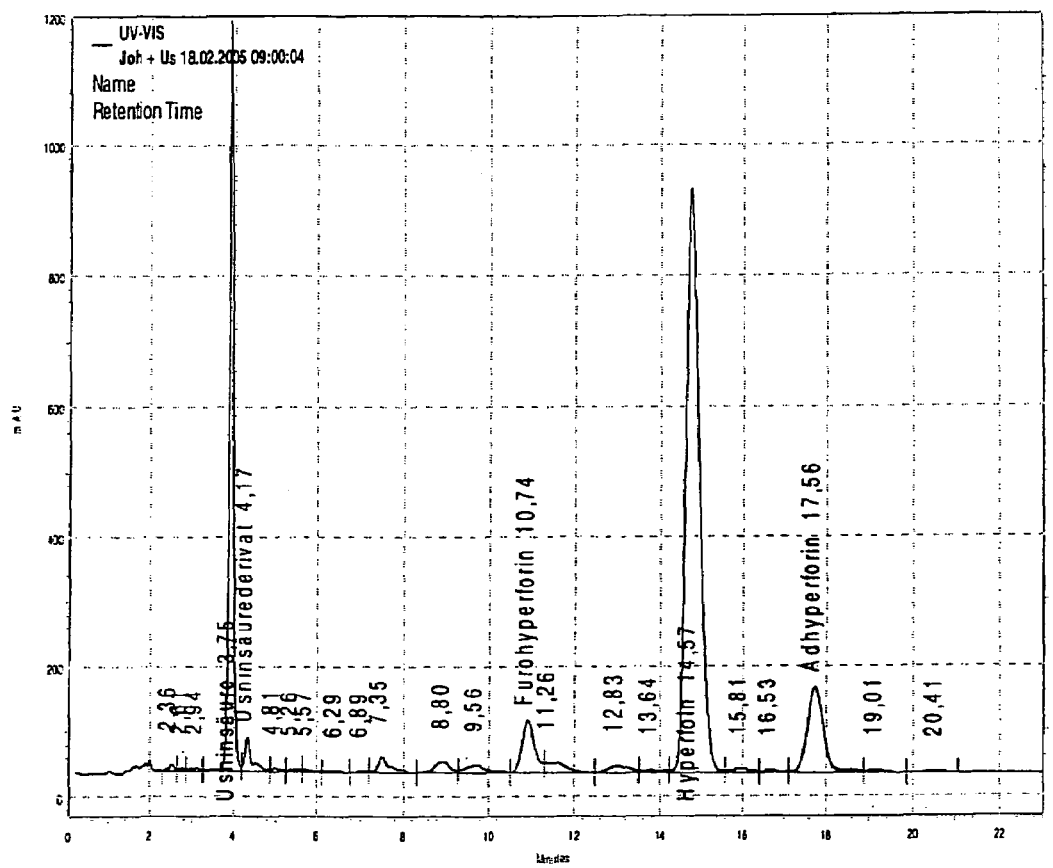
FIG. 3 shows an HPLC chromatogram of a $CO_2$ extract in which St. John's Wort and old man's beard were homogenised together.
Figure 4:
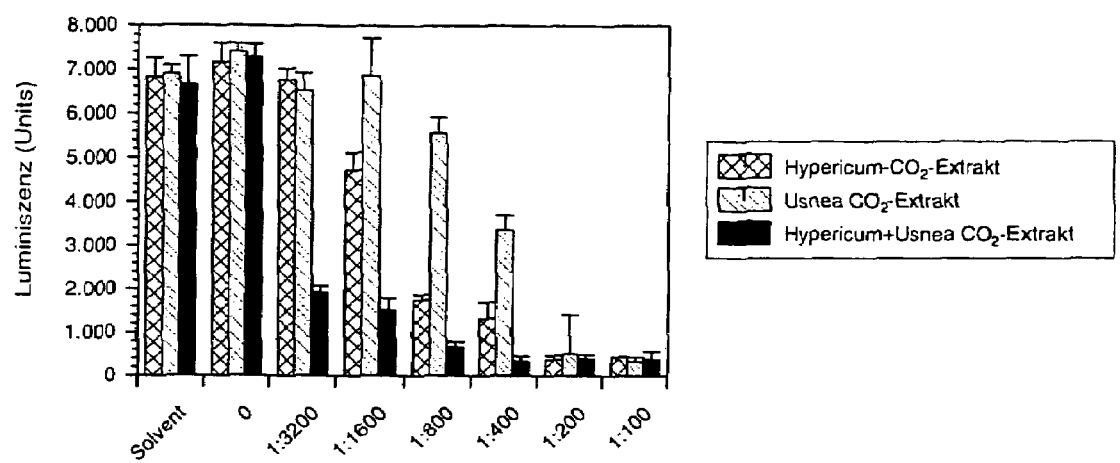
FIG. 4 shows the antiproliferative effect of $CO_2$ extracts, a *Hypericum* $CO_2$ extract, a *Usnea* $CO_2$ extract and a $CO_2$ extract which was isolated from *Hypericum* and *Usnea* having been used. The values were measured in the ATP assay (ViaLight) on the basis of the luminescence.

Potentiation of the Antiproliferative Effect by Combination of *Hypericum* Extract and *Usnea* Extract Inhibition of the proliferation of activated lymphocytes may be an expression of an anti-inflammatory effect of substances. The antiproliferative effect of *Usnea* extract was therefore investigated. In addition, an investigation was carried out to determine whether *Usnea* extract can enhance the known antiproliferative effect of a St. John's Wort (*Hypericum*) $CO_2$ extract. For this purpose, lymphocytes of the peripheral blood (PBMC) were isolated by a Ficoll density gradient and sown in microtiter plates in a cell count of 100 000/ml. Thereafter, the cells were stimulated with 1 µg/ml of PHA (phytohaemagglutinin) and incubated with or without addition of plant extracts or solvent controls for 24 h. The following stock solutions were prepared: 25% *Usnea* extract and 70% EtOH, 25% *Hypericum* extract in EtOH, 12.5% *Usnea* extract+12.5% *Hypericum* extract in EtOH. All stock solutions were used in a dilution series of: 1:100 to 1:3200. Thereafter, the cell proliferation was determined by measurement of the ATP content (ViaLight). Half the inhibitory concentration (IC50) of *Usnea* extract occurred at a dilution of 1:400. It was surprisingly found that the addition of *Usnea* extract to the *Hypericum* extract not only had an additive effect but potentiated the antiproliferative effect thereof (FIG. 4).

EXAMPLE 3

Anti-Inflammatory Effect in UV Erythema Test

The minimal erythema dose for UVB was determined in the case of seven healthy test persons. Thereafter, test fields on the back were exposed to 1.5 times the minimal erythema dose (MED). The test substances were applied in Finn chambers for 24 hours. The UV-induced erythema was determined photometrically before exposure and after action of the substances. It was found that 5% *Usnea* extract can inhibit the UV-induced inflammation as well as the cortisone preparation Prednicarbate (Dermatop®) (FIG. 5).

EXAMPLE 4

Stabilization of Hyperforin by Addition of *Usnea* Extract

It was surprisingly found that the combination of a St. John's Wort extract standardised to 10% hyperforin with a *Usnea* extract standardised to 4% usnic acid leads to an increase in the stability of hyperforin by 100% when incorporated into an aqueous gel comprising propylene glycol (Table 3).

Table 3 shows the stabilizing effect of a *Usnea* $CO_2$ extract on a $CO_2$ extract of St. John's Wort. In Table 3, it is clear that the proportion of hyperforin is almost twice as high if *Usnea* $CO_2$ extract was added. This time-related stabilisation is very important for pharmaceutical and cosmetic products since these should be stable for as long as possible without degradation of the active substances.

TABLE 3

Stabilisation of hyperforin by addition of *Usnea* extract:

| | shortly after preparation | | after 8 weeks | |
|---|---|---|---|---|
| | with *Usnea* | without *Usnea* | with *Usnea* | Without *Usnea* |
| Hyperforins | 43% | 42% | 36% | 18% |
| other components and hyperforin degradation products | 57% | 58% | 64% | 82% |

EXAMPLE 5

Stabilisation of Hyperforin in the Light Exposure Test by the Combination of *Hypericum* Extract and *Usnea* Extract The *Usnea-Hypericum* concentrate preferred according to the invention and preformulated by means of a colloid mill was dissolved in the preferred concentration of 2% in MCT oil in order to simulate a ready-to-use end product. The hyperforin content of the end formulation was determined as 0.305%. In comparison, the identically prepared preformulation without *Usnea* extract, comprising only *Hypericum*, was likewise dissolved in a concentration of 2% in MCT oil, a hyperforin content of 0.313% being measured in the end formulation. 5 g of each of the two low-viscosity oil formulations were poured on to a glass plate, where they form a thin film having a layer thickness of about 1 mm. Both glass plates were exposed to daylight in the open air, the thin oil film providing a large area of attack for light and oxygen. Samples of the oil film on both plates were taken at certain time intervals and the hyperforin content was measured by means of HPLC. In this way, the hyperforin degradation in both end formulations can be monitored. At the end of the measurement series, a content of 0.057% of hyperforin was found in the formulation without *Usnea*, comprising only *Hypericum*, while the hyperforin content in the *Hypericum-Usnea* preparation after the same time span was more than twice as high at 0.117%. This once again confirms the better stability of hyperforin in the *Hypericum-Usnea* complex even in dilute application formulation.

EXAMPLE 6

Inhibition of UV-Induced Prostaglandin $E_2$ ($PGE_2$) Production by *Usnea* Extract HaCaT Keratinocytes (100 000/ml) were cultivated in Petri dishes with cell culture medium (RPMI with 10% FBS) to confluence. Thereafter, the medium was replaced by phosphate buffer and the cyclooxygenase saturated by addition of arachidonic acid (AA). One batch was left in the dark and one batch was exposed to 30 mJ/cm² UVB. After addition of medium and addition of *Usnea* extract in different concentrations, both batches were incubated for 24 h. Thereafter, the supernatants were removed and the production of $PGE_2$ was measured by means of a $PGE_2$ ELISA (R&D Systems).

FIG. 6 shows the dose-dependent inhibition of the UV-induced prostaglandin synthesis by *Usnea* extract.

EXAMPLE 7

Inhibition of the UV-Induced Increase of Matrix Metalloproteinase (MMP-1) by *Usnea* Extract and the Combination of *Usnea* Extract and *Hypericum* Extract Primary human fibroblasts were isolated by enzymatic digestion from human skin and cultivated in cell culture medium (DMEM with 10% FBS) over several passes in Petri dishes. Thereafter, 100 000 cells/ml were sown in Petri dishes and incubated after adherence with medium, *Usnea* extract and *Hypericum* extract. In one batch, the medium was replaced by phosphate buffer and the cells were exposed to 60 J/cm² UVA-1. After addition of medium, a part of the exposed cells was incubated with *Usnea* extract or the combination of *Usnea* extract and *Hypericum* extract in a concentration of 0.1% v/v in each case for 24 h. Thereafter, the cells were lysed on ice and the activity of the MMP-1 was determined by measurement using an MMP-1 enzyme activity assay (R&D Systems).

FIG. 7 shows the inhibition of the UV-induced increase of matrix metalloproteinase-1 (MMP-1) by *Usnea* extract and the potentiation of the effect by combination of *Usnea* extract and *Hypericum* extract.

Moreover, FIG. 5 shows the anti-inflammatory effect of a *Usnea* $CO_2$ extract which was applied in a concentration of 5% in an aqueous gel to the skin of the test persons. An inflammation caused by UVB radiation can therefore be treated by the pharmaceutical composition according to the invention. The pharmaceutical composition according to the invention is therefore also suitable for the treatment of inflammations caused by excessive exposure to sunlight (sunburn).

EXAMPLE 8

Use of *Usnea* Gel and *Usnea/Hypericum* Gel in Common Acne

In the case of 3 patients, the facial skin lesions healed within two weeks as a result of the use of a gel according to the invention as described in preparation example 1.

The results are shown in Table 4.

TABLE 4

|  | Age, sex | Before treatment | After two weeks |
|---|---|---|---|
| Patient 1 | 30 years, male | common acne | improved |
| Patient 2 | 24 years, female | acne papulopustuolosa | cured |
| Patient 3 | 56 years, female | rosacea | cured |

The invention claimed is:

1. A pharmaceutical composition comprising 0.01-10% by weight of a $CO_2$ extract of *Usnea barbata* and 0.01-20% by weight of a $CO_2$ extract of *Hypericum perforatum*.

2. The pharmaceutical composition according to claim 1 comprising 0.11-10% by weight of a $CO_2$ extract of *Usnea barbata* and 0.11-10% by weight of a $CO_2$ extract of *Hypericum perforatum*.

3. The pharmaceutical composition according to claim 1 comprising 0.5-5% by weight of a $CO_2$ extract of *Usnea barbata* and 0.5-5% by weight of a $CO_2$ extract of *Hypericum perforatum*.

4. The pharmaceutical composition according to claim 1, wherein the $CO_2$ extract of *Usnea barbata* contains 3-6% by weight of usnic acid.

5. The pharmaceutical composition according to claim 1, wherein the $CO_2$ extract of *Usnea barbata* contains at least 85% by weight of usnic acid.

6. The pharmaceutical composition according to claim 1, wherein the $CO_2$ extract of *Hypericum perforatum* contains 5-15% by weight of hyperforin.

7. The pharmaceutical composition according to claim 1, wherein the $CO_2$ extract of *Hypericum perforatum* contains at least 40% by weight of hyperforin.

8. The pharmaceutical composition according to claim 1, wherein said composition is an aqueous gel.

9. The pharmaceutical composition according to claim 1, wherein said composition is a lotion.

10. The pharmaceutical composition according to claim 1, wherein said composition is an ointment.

11. The pharmaceutical composition according to claim 1, wherein said composition is a stiffened gel which can be used in the form of a pen.

12. The pharmaceutical composition according to claim 1, wherein said composition is a powder.

13. A method for treating acne comprising topically administering to a subject in need thereof, the composition according to claim 1.

14. The method of claim 13, wherein said acne is acne papulopustuolosa.

15. A method for treating rosacea comprising topically administering to a subject in need thereof, the composition according to claim 1.

* * * * *